(12) United States Patent
de la Brousse et al.

(10) Patent No.: US 6,432,654 B1
(45) Date of Patent: Aug. 13, 2002

(54) DRUG SCREENS FOR REGULATORS OF THE EXPRESSION OF THE OBESE GENE

(75) Inventors: Fabienne Charles de la Brousse, San Francisco; Jin-long Chen, Millbrae, both of CA (US)

(73) Assignee: Tularik Inc, South South Francisco, CA (US)

( * ) Notice: Subject to any disclaimer, the term of this patent is extended or adjusted under 35 U.S.C. 154(b) by 0 days.

(21) Appl. No.: 09/114,552

(22) Filed: Jul. 13, 1998

Related U.S. Application Data

(62) Division of application No. 08/707,408, filed on Sep. 4, 1996, now Pat. No. 5,780,258.

(51) Int. Cl.$^7$ ............................................. G01N 33/567
(52) U.S. Cl. ....................................... 435/7.21; 800/18
(58) Field of Search ..................... 800/18, 14; 435/7.21

(56) References Cited

U.S. PATENT DOCUMENTS 5,741,666 A * 4/1998 Tartaglia .................... 435/69.1

OTHER PUBLICATIONS

Bradley et al. Modifying the mouse: Design and desire. Biotechnology. vol. 10, pp. 534–539, see entire document, May 1992.*
Seamark. Progress and emerging problems in livestock transgenesis: a summary perspective. Reproductive fertility and development. vol. 6, pp. 653–657, see abstract and p. 654, col. 2, para 3, Feb. 1995.*
Mullins and Mullins. Trangenesis in the rat and larger mammals. Journal of Clinical Investigation. vol. 98, Supplement, pp. S37–S40, see entire document, Apr. 1996.*
Capecchi. Targeted gene replacement. Scientific American. vol. 270, pp. 34–41, especially p. 36, Mar. 1994.*
Kitamoto et al. Humanized prion protein knock–in by cre–induced site–specific recombination in the mouse. Biochemical and Biophysical Research Communications. vol. 222, pp. 742–747, especially p. 744 para. 1, Jun. 1996.*
Kress et al. Hox–2.3 upstream sequences mediate IacZ expression in intermediate mesoderm derivatives of transgenic mice. Development. vol. 109, pp. 775–786, see e.g. abstract, Aug. 1990.*
Dubuc. The development of obesity, hyperinsulinemia, and hyperglycemia in ob/ob mice. Metabolism vol. 25, pp. 1567–1574, abstract only, Dec. 1976.*
Halass et al. Weight–reducing effects of the plasma protein encoding by the obese gene. Science. vol. 269, pp. 543–549, see e.g. abstract, Jul. 1995.*
Cusin et al. The ob gene and insulin. Diabetes vol. 44, pp. 1467–1470, see e.g. abstract, Dec. 1995.*
Sista et al. A cell–based reporter for the identification of protein kinase C activators and inhibitors. Molecular and Cellular Biochemistry. vol. 141, pp. 129–134, abstract only, Dec. 1994.*

\* cited by examiner

*Primary Examiner*—James Ketter
*Assistant Examiner*—Richard Schnizer
(74) *Attorney, Agent, or Firm*—Richard Aron Osman

(57) ABSTRACT

The invention provides methods and compositions for screening for pharmacological agents which regulate satiety, fat metabolism and/or the type II diabetes mellitus in mammals, and in particular, agents active at regulating the level of ob gene expression. An exemplary assay involves (a) contacting a mammalian adipocyte comprising a mutant of a native ob allele encoding a reporter of ob gene expression, wherein the expression of the reporter is under the control of the gene expression regulatory sequences of the native ob allele, with a candidate agent under conditions whereby but for the presence of the agent, the reporter is expressed at a first expression level; and, (b) measuring the expression of the reporter to obtain a second expression level, wherein a difference between the first and second expression levels indicates that the candidate agent modulates ob gene expression. Preferred methods include cell-based transcription assays using adipocytes from transgenic animals having a "knock-in" luciferase reporter at least one ob allele.

5 Claims, 1 Drawing Sheet

DRUG SCREENS FOR REGULATORS OF THE EXPRESSION OF THE OBESE GENE

This is a divisional application of U.S. Ser. No. 08/707,408, filed Sep. 4, 1996, now U.S. Pat. 780,258, which is incorporated herein by reference.

FIELD OF THE INVENTION

The field of this invention is cell-based drug screens for regulators of the expression of the obese gene.

BACKGROUND

Satiety in vertebrates is controlled by a blood-borne hormone encoded by the obese (Ob) or leptin gene. Homozygous recessive mutations of the Ob gene (ob/ob) lead to the gross expansion of adipose tissue. Since animals lacking a functional Ob gene become phenotypically obese, it has been predicted that the Ob gene product plays a central role in energy homeostasis and appetite suppression.

The Ob gene has recently been cloned, facilitating molecular characterization of its encoded protein. The Ob gene product, termed leptin, is a secreted polypeptide produced by adipose tissue. Fat tissue accumulates in response to the intake of excess energy stores, becoming grossly expanded in animals lacking either functional leptin or its putative receptor. Under such circumstances, expression of the Ob gene is markedly elevated. These observations give evidence of a feedback loop responsible for controlling vertebrate energy balance. Adipose tissue subsides under conditions of food deprivation, resulting in a reduced level of leptin production and a corresponding increase in appetite. In the well-fed state, excess energy stores accumulate in adipose tissue. Upon maturation and expansion, adipocytes activate expression of the Ob gene, whose product then serves to quell satiety and stimulate metabolic activity.

Several lines of evidence have indicated that leptin production may be regulated at the level of transcription of its encoding gene. Adipose tissue derived from homozygous Ob-defective animals contains appreciably higher levels of leptin mRNA than that of either heterozygous or wild-type controls. Increased levels of Ob mRNA have also been observed in obese humans. Furthermore, expression of the Ob gene is elevated in response to insulin and other blood borne hormones involved in energy homeostasis. Finally, thiazolinedione derivatives, used to reduced insulin resistance in non-insulin dependent diabetes, have been shown to reduce Ob gene expression. These observations provide evidence that expression of the Ob gene is sensitively balanced with respect to the supply of metabolic energy stores as well as the hormonal factors responsible for controlling energy homeostasis.

RELEVANT LITERATURE

Zhang, Y., et al. (1994) Nature 372, 425–432 report the cloning of the Ob gene. de la Brousse et al. (1996) PNAS 93, 4096–4101, He et al. (1995) J. Biol Chem 270, 28887–28891, Hwang et al. (1996) PNAS 93, 873–877, Gong et al. (1996) J. Biol Chem 271, 3971–3974, report the identification of transcriptional control elements of the ob gene.

SUMMARY OF THE INVENTION

The invention provides methods and compositions for screening for agents which regulate the level of ob gene expression. Such agents find use in modulating a wide variety of physiological manifestations of ob gene expression including satiety, fat metabolism, disease states such as obesity, type II diabetes mellitus, etc.

The subject assays are cell-based and generally involve (a) contacting a mammalian adipocyte comprising a mutant of a native ob allele encoding a reporter of ob gene expression, wherein the expression of the reporter is under the control of the native gene expression regulatory sequences of the native ob allele, with a candidate agent under conditions whereby but for the presence of the agent, the reporter is expressed at a first expression level; and, (b) measuring the expression of the reporter to obtain a second expression level, wherein a difference between the first and second expression levels indicates that the candidate agent modulates ob gene expression.

The mutant may result from replacement of a portion of said native ob allele with a sequence encoding said reporter. For example, the adipocyte may be a progeny of a genetic knock-in cell made by homologous recombination of the native ob allele with a transgene comprising a sequence encoding the reporter flanked by flanking sequences capable of effecting the homologous recombination of the transgene with the native ob allele, a positive selectable marker positioned inside the flanking sequences and a negative selectable marker positioned outside the flanking sequences. The adipocyte may be a primary adipocyte residing in or isolated from an animal transgenic in the mutant or derive from a cultured cell line transgenic in the mutant. Preferred methods are ex-vivo cell-based transcription assays using adipocytes from transgenic animals having a "knock-in" luciferase reporter at least one ob allele.

The invention also encompasses mammalian adipocytes and mammals transgenic in a mutant of a native ob allele encoding a reporter of ob gene expression, wherein the expression of the reporter is under the control of the gene expression regulatory sequences of the native ob allele, genetic knock in vectors for making such animals and cells and methods of making and using such vectors, cells and animals.

DETAILED DESCRIPTION OF THE INVENTION

Figure 1:
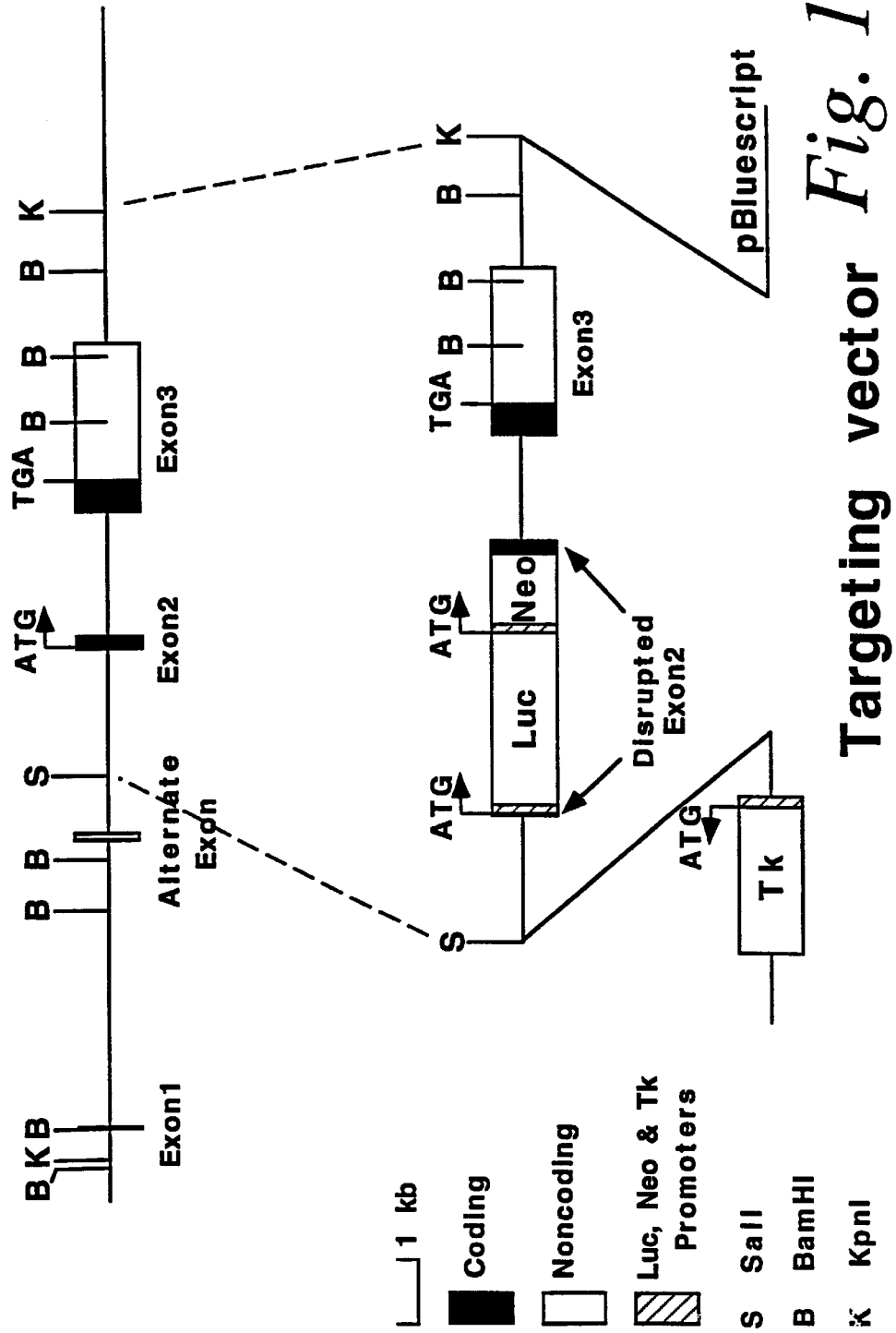
FIG. 1 shows the structures of the mouse ob gene and an exemplary "knock in" targeting vector.

The general assays involve contacting a cell having a reporter for ob gene expression with a candidate agent and monitoring reporter expression to determining if the agent has a specific effect on ob gene expression. To accurately reflect ob gene expression, the reporter gene is positioned within native ob gene such that effects of the mutation on transcription and translation at the locus, as compared with the corresponding wild-type ob allele, are minimized. Generally, all the native ob gene sequences 5' and 3' to the native ob transcriptional start and stop sites are retained in the mutant allele, as are preferably all the native ob sequences 5' and 3' to the native ob translational start and termination sites. Hence, the transcriptional and translational start and termination sites of the native ob gene are preferably retained and use for the reporter. The reporter may be encoded at the ob translational start site which is generally in the second exon, or in frame within the ob structural gene. Hence, the reporter may be expressed free or as a fusion product with N- and/or C-terminal ob sequences, e.g. the reporter gene may be an insertion or partial replacement of ob sequence in the second and or third exon. The size and structure of the reporter transcript preferably approximates the native ob transcript.

Preferred reporter genes are readily expressed by the host cells and provide products that are readily detected and quantified. Exemplary reporter genes include beta galactosidase, CAT and, preferably, luciferase. The mutated ob locus may also comprise a positive selection marker such as an antibiotic resistance gene, residual from the initial construction of the mutation. Alternatively, such residual sequences may be lost or removed in the course of cell passage or animal reproduction.

The cells used in the assays are adipocytes, which refers to cells which are at least partially differentiated toward mature adipocytes. Such cells are identified by any of adipocyte-specific gene expression (e.g. ob gene expression), adipocyte-specific markers, or morphology. The cells may be a progeny of a genetic knock-in cell made by homologous recombination, e.g. recombination of the native ob allele with a transgene comprising a sequence encoding the reporter flanked by flanking sequences capable of effecting the homologous recombination of the transgene with the native ob allele, a positive selectable marker positioned inside the flanking sequences and a negative selectable marker positioned outside the flanking sequences (see Experimental Section, below). The adipocyte may be a primary adipocyte isolated from an animal transgenic in the mutant or derive from a cultured cell line transgenic in the mutant. Such cell lines may be made by gene targeting into established apidogenic cell lines such as 3T3-L1, 3T3-F442A, OB17, HGFU, OB1771, 1246, A31T, TAI and ST13, derived from the transgenic animal disclosed herein and immortalized, etc.

Animals transgenic in the reporter/ob constructs may be used directly in studies to ascertain the effect of various stimuli, such as physical activity, diet, sleep patterns, pharmacological intervention, etc., on ob gene expression. Alternatively, primary adipocytes can be isolated as describe below for ex vivo drug screening.

An exemplary assay involves (a) contacting a mammalian adipocyte (ex vivo for high throughput applications) comprising a mutant of a native (i.e. otherwise naturally present in the host cell or animal) ob allele encoding a reporter of ob gene expression, wherein the expression of the reporter is under the control of the native gene expression regulatory sequences (preferably both transcription and translational regulatory elements) of the native ob allele, with a candidate agent under conditions whereby but for the presence of the agent, the reporter is expressed at a first expression level; and, (b) measuring the expression of the reporter to obtain a second expression level, wherein a difference between the first and second expression levels indicates that the candidate agent modulates ob gene expression.

EXPERIMENTAL

1. Transgenic Primary Adipocytes

Approximately 20 ug of a pBluescript gene-targeting construct containing about 2 kb of 5' flanking sequence and about 7 kb of 3' flanking sequence of the second exon of the second exon of the ob gene was electroporated into D3 ES cells using a Bio-Rad gene pulser set at 25 uF/350 V. The construct effects the replacement of the second exon with a cassette containing the luciferase reporter and the neomycin resistance genes (FIG. 1). The construct also contained a thymidine kinase negative selection marker outside the cassette. After 9 days selection in 180 ug/ml G418 and 2 uM gancyclovir, drug-resistant clones were placed into 24-well plates and expanded in culture. Screening for correctly targeted clones was done by Southern analysis and suitable clones were injected into 3.5 day postcoital BALB/c blastocysts to generate chimeras. Heterozygote germline transmissions are identified by Southern analysis and bred as a stable strain. These are also intercrossed to yield homozygotes for the ob mutation.

To isolate primary adipocytes for screening assays, epididymal fat tissue is excised from two month old mice and prepared for cell culture by collagenase digestion as described in Rolland et al. (1995) J. Biol Chem 270, 1102–2206. After digestion, primary adipocytes are isolated by filtration through 180 um sieves, also as described by Rolland et al. (supra).

2. Transgenic Cultured Adipocyte Cell Lines

The pBluescript gene-targeting construct described above and shown in FIG. 1 is electroporated into 3T3-F442A cells using a Bio-Rad gene pulser set at 25 uF/350 V. After approximately 14 days of positive/negative selection in 180 ug/ml G418 and 2 uM gancyclovir, drug-resistant clones were placed into 24-well plates and expanded in culture. Screening for correctly targeted clones was done by Southern analysis.

To obtain differentiated cells for screening assays, grow initial cultures of 50% confluent cells to 100% confluence, then continue incubation 10–14 days to obtain maximal differentiation.

3. Cell-based Transcription Assay.

Aliquot 100 ul cell suspension ($10^4$–$10^5$ primary or cultured, differentiated adipocytes) into each well of 96-well plate under sterile conditions Add compound or extract to 10 uM final concentration Incubate 6–18 hrs at 37° C.

Remove incubation media

Add 100 ul lysis/luciferin buffer containing 1.0% non-ionic detergent (Triton x-100), 530 uM ATP, 270 uM coA and 470 uM luciferin (Promega).

Measure luciferase-derived luminescence on automated Torcon AML-34 and 7710 Microplate Luminometer (Cambridge Technologies, Inc.) luminometers.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated genetic knock-in primary mammalian adipocyte isolated from a trasgenic mouse, wherein the adipocyte is a progeny of a genetic knock-in cell made by homologous recombination of a native ob allele with a transgene comprising a sequence encoding a reporter flanked by flanking sequences which effect, in conjunction with the cell, the homologous recombination of the transgene with the naive ob allele, whereby the transgene resides on a chromosome in the trasngenic mouse, wherein the expression of the reporter is under the control of native gene expression regulatory sequences of the native ob allele.

2. The adipocyte of claim 1, wherein the knock-in cell results from the replacement of a portion of the native ob allele with a sequence encoding the reporter.

3. The adipocyte of claim 1, wherein the reporter is luciferase.

4. A cell-based method for screening for modulators of ob gene expression, the method comprising steps:

(a) determining a first reporter expression level in a first isolated mammalian adipocyte according to claim 1, (b) contacting a second isolated mammalian adipocyte according to claim 1 with a candidate agent under conditions whereby but for the presence of the agent, the reporter is expressed at the first reporter expression level;

(c) determining a second reporter expression level in the second isolated mammalian adipocyte; and (d) comparing the first expression level with the second expression level, wherein a difference between the first and second expression levels indicates that the candidate agent modulates ob gene expression.

5. The method of claim 4, wherein the second adipocyte is in a suspension of identical adipocytes, the reporter is luciferase, the contacting step comprises depositing aliquots of the suspension into wells of a plate under sterile conditions, adding the agent to the aliquots and incubating the aliquots 6–18 hours, and the measuring step comprises adding a lysing detergent, ATP, coA and luciferin to the aliquots and measuring luciferase-derived luminescence.

* * * * *